US00PP33490P2

(12) United States Plant Patent
Palmer

(10) Patent No.: US PP33,490 P2
(45) Date of Patent: Sep. 14, 2021

(54) ***RUDBECKIA* PLANT NAMED 'G16223'**

(50) Latin Name: *Rudbeckia hirta*
Varietal Denomination: G16223

(71) Applicant: Garden Genetics, Bellefonte, PA (US)

(72) Inventor: Irene E. Palmer, Arden, NC (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 16/940,575

(22) Filed: Jul. 28, 2020

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
CPC ... A01H 5/02; A01H 5/00; A01H 6/14; A01H 6/088
See application file for complete search history.

*Primary Examiner* — June Hwu
(74) *Attorney, Agent, or Firm* — Cassandra Bright

(57) ABSTRACT

A new and distinct cultivar of *Rudbeckia hirta* plant named 'G16223' is disclosed, characterized by strong, dense branching on plants reaching approximately 15 to 18 inches tall. Inflorescences have stiff ray florets held horizontally and are held on short peduncles. Young flowering plants produce single flowers, and mature plants produce an extra row of ray florets. Ray florets are golden yellow with a dark greyed-purple base, forming a dark eye. The new variety is a *Rudbeckia*, and is normally used as a garden or container plant.

3 Drawing Sheets

Latin name of the genus and species: *Rudbeckia hirta.*
Variety denomination: 'G16223'.

BACKGROUND OF THE INVENTION

The new cultivar is the product of a planned hybridization by the inventor. The crossing resulting in the new variety was made in October 2015 at a nursery in Bellefonte, Pa. The new variety was found and selected by the inventor in July 2016 at the same nursery in Bellefonte, Pa.

Asexual reproduction of the new cultivar 'G16223' by terminal vegetative cuttings was performed at the same nursery in Bellefonte, Pa. in August 2016. Subsequently, asexual reproduction has shown that the unique features of this cultivar are stable and reproduced true to type through successive generations.

SUMMARY OF THE INVENTION

The cultivar 'G16223' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G16223'. These characteristics in combination distinguish 'G16223' as a new and distinct *Rudbeckia hirta* cultivar:

1. Single flowers with an extra row of flower petals developing as plant matures
2. Golden yellow ray florets, with a bright crimson "eye" formed by a lower ray floret coloration of greyed-purple.
3. Stiff ray florets held stiffly horizontal
4. Strong, dense branching
5. Short peduncles
6. 15-18" tall

PARENT COMPARISON

Plants of the new cultivar 'G16223' are similar to plants of the seed parent variety, the unpatented *Rudbeckia* '1002-1', in most horticultural characteristics. However, plants of the new cultivar 'G16223' differ in the following ways:

1. Seed parent is dwarf and compact; new variety is intermediate in height.
2. Seed parent has small clear gold ray florets; new variety has large golden yellow ray florets with a crimson red eye.
3. Seed parent has moderate branching; new variety is more densely branched.
4. Seed parent stops growing once the flowers senesce; new variety continues to grow and flower.

Plants of the new cultivar 'G16223' are similar to plants of the pollen parent variety, the unpatented *Rudbeckia* '7016-5', in most horticultural characteristics. However, plants of the new cultivar 'G16223' differ in the following ways:

1. Pollen parent has red-violet ray florets with a darker eye; new variety has golden yellow ray florets with a crimson red eye.
2. Pollen parent is intermediate in height, 18-24" tall; new variety is shorter, 15-18" in height.
3. Pollen parent is semi-double flowered; 'G16223' is single-flowered as a young plant and develops a second layer of ray florets as the plant matures, providing a very unique appearance.

COMMERCIAL COMPARISON

'G16223' can be compared to the commercially known variety *Rudbeckia hirta* 'Balrudosh', U.S. Plant Pat. No.

25,496. These plants are similar in most horticultural characteristics. However, plants of the new cultivar 'G16223' differ in the following ways:

1. 'Balrudosh' has fully double-type inflorescences; 'G16223' has single to semi-double inflorescences.
2. 'Balrudosh' has streaked ray florets; 'G16223' has un-streaked bi-color ray florets.
3. 'Balrudosh' typically has medium-green leaves; 'G16223' has dark-green leaves.
4. 'Balrudosh'has a moderately vigorous, upright habit; 'G16223' is more compact and more densely branched.

'G16223' can also be compared to the commercially known variety *Rudbeckia hirta* 'RUDHT37', U.S. Plant Pat. No. 30,657. These plants are similar in most horticultural characteristics. However, plants of the new cultivar 'G16223' differ in the following ways:

1. 'RUDHT37' has a broad, upright habit; 'G16223' is more densely branched and more compact.
2. 'RUDHT37' has single inflorescences, inflorescences of 'G16223' begin as single but develop an additional row of ray florets as the plant matures to produce a semi-double form.
3. 'RUDHT37' ray florets are yellow-orange; 'G16223' ray florets are golden yellow, with a crimson-red blotch at the base of each ray floret, creating a distinct "eye".

BRIEF DESCRIPTION OF THE PHOTOGRAPHS

The accompanying photograph in FIG. 1 illustrates in full color a typical plant of 'G16223' grown in a greenhouse in Bellefonte, Pa. The plant is approximately 4 months old in a 1 gallon pot. Inflorescences illustrated in FIG. 1 are on a young plant, and produce a single row or ray florets.

Figure 1:
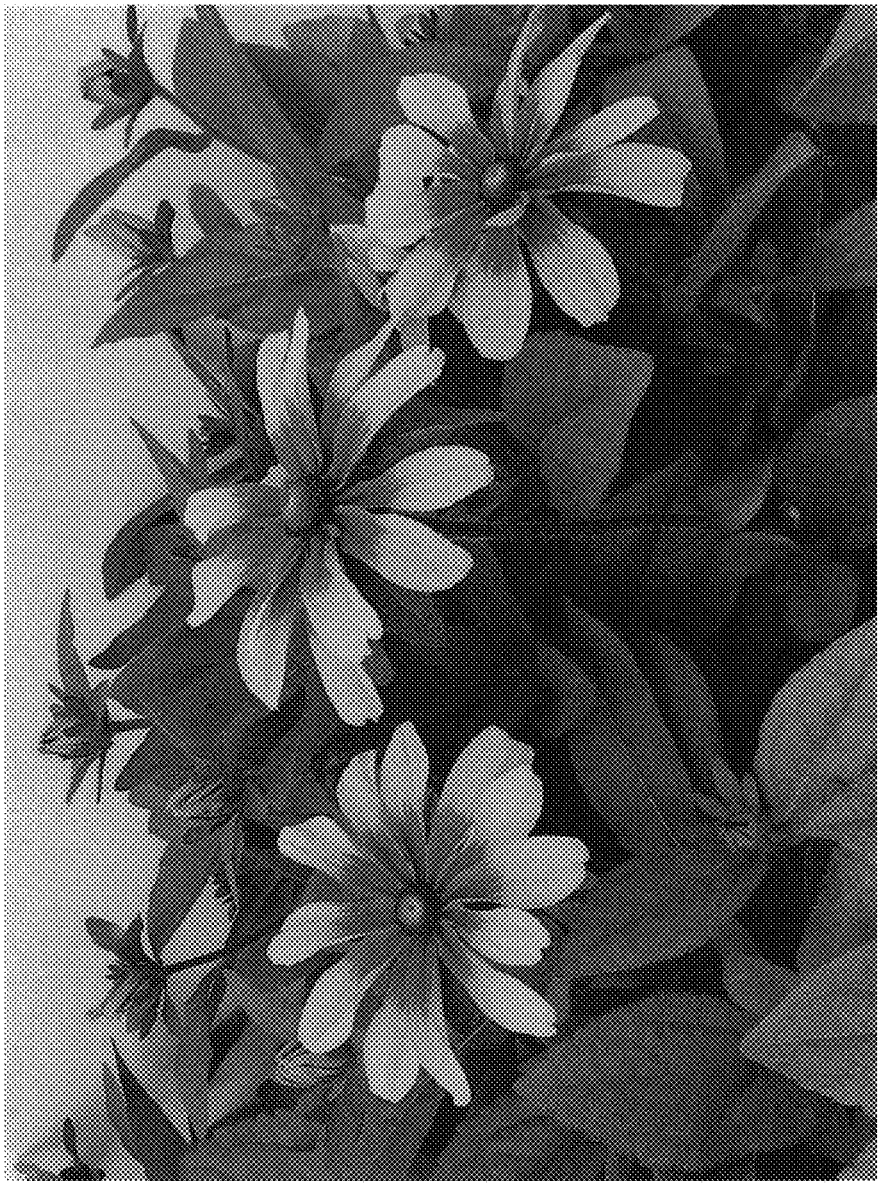
Figure 2:
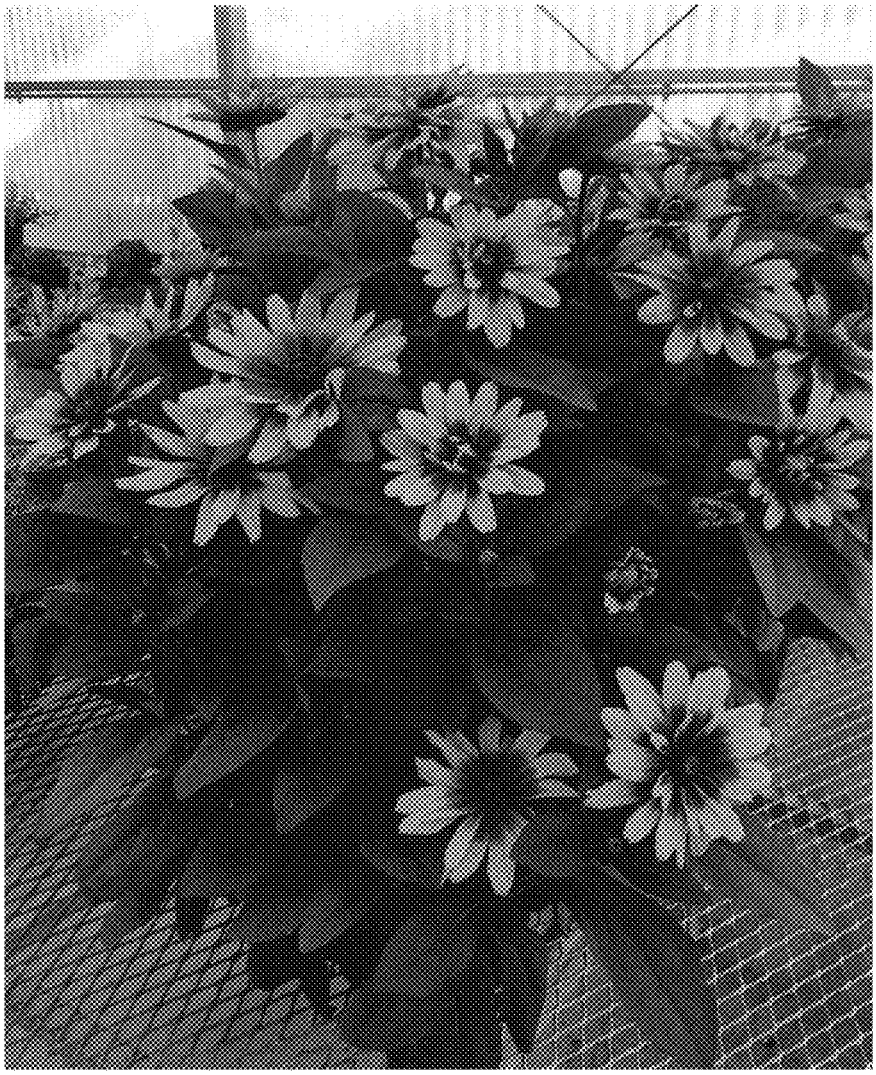
FIG. 2 illustrates an older plant, around 9 months in a greenhouse, with a second row of ray florets developing.
Figure 3:
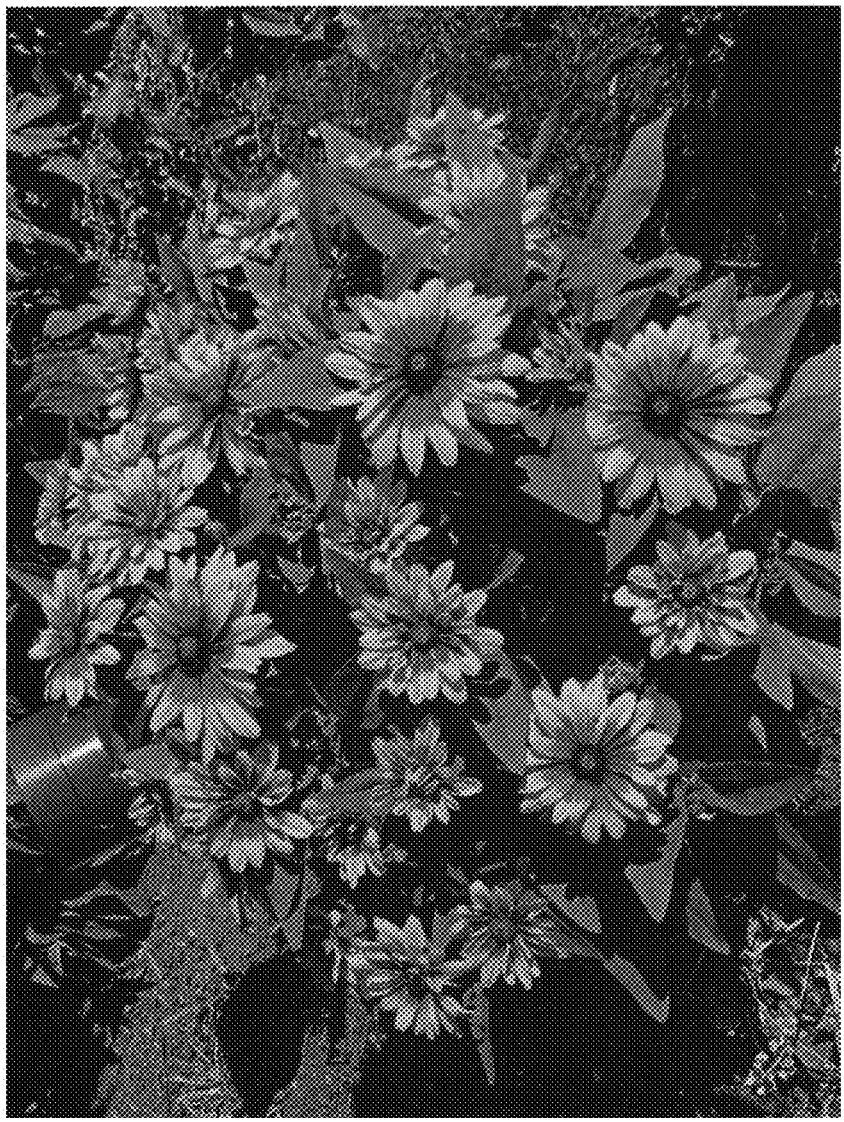
FIG. 3 illustrates a plant of approximately 18 months overwintered outdoors in Bellefonte, Pa.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'G16223' plants grown outdoors from Spring to early Summer in Camarillo, Calif. The growing temperature ranged from about 7° C. to 30° C. during the day and from about 5° C. to 12° C. during the night. General light conditions are bright, normal sunlight. Measurements and numerical values represent averages of typical plant types. Plants are approximately 5 to 6 months old from a rooted cutting. No chemical or photoperiodic treatments were given.

Botanical classification: *Rudbeckia hirta* 'G16223'.

PROPAGATION

Time to initiate rooting: 7 to 10 days at approximately 25° C.

Time to produce a young rooted liner: Approximately 40 days at approximately 22° C.

Root description: Fine, well-branched, fibrous, becoming slightly woody with age.

PLANT

Growth habit: Hardy, herbaceous perennial. Compact v-shaped or globular. Plants are moderately dense based on quantity of foliage, stems and flowers. Plants are moderately to strongly floriferous.

Height:

*To top of foliar plane*.—Approximately 35-45 cm.

*To top of flowering plane*.—Approximately 45 to 55 cm.

Plant spread: Approximately 50 cm.

Growth rate: Moderate.

Branching characteristics: Basal and low lateral branching. Well branched.

Length of branches: Approximately 18 to 35 cm, excluding peduncle.

Diameter branches: Approximately 5 to 6 mm.

Quantity of branches: Approximately 4 to 6 basal branches, each basal branch with 2 to 4 lateral branches.

Texture of lateral branches: Hispid. Hairs about 3 mm long, colored near White 155A.

Color of lateral branches: Near RHS Green 143C. Emerging branches near internodes flushed Greyed-Purple N186C.

Aspect: Approximately 10° to 15° angle from base of plant.

Strength of lateral branches: Very strong.

Internode length: Average range 4.5 to 5.5 cm.

Age of plant described: Approximately 5 to 6 months old.

FOLIAGE

Arrangement: Flowering stems produce sub-opposite or alternate occurring foliage. Basal foliage occurs in irregular whorls.

*Average length*.—Average range 10 to 12 cm.

*Average width*.—Average range 3.5 to 4.5 cm.

*Shape of blade*.—Young foliage elliptic, older foliage spatulate.

*Apex*.—Acute.

*Base*.—Attenuate.

*Attachment*.—Sessile.

*Margin*.—Dentate and densely ciliate.

*Texture of top surface*.—Densely pilose to nearly hirsute, hairs stiff, but, soft. Average hair length approximately 2 mm, colored near RHS White 155A.

*Texture of bottom surface*.—Densely pilose to nearly hirsute, hairs stiff, but, soft. Average hair length approximately 2 mm, colored near RHS White 155A.

*Foliage color, cauline and basal leaves*.—Young foliage upper side: Near RHS Green 143C. Young foliage under side: Near RHS Yellow-Green 144A. Mature foliage upper side: Near RHS Green 137B. Mature foliage under side: Near RHS Green 137D.

*Venation*.—Type: Pinnate. Venation color upper side: Near RHS Yellow-Green 144D. Venation color under side: Near RHS Yellow-Green 145C.

INFLORESCENCE

Bloom period: Naturally blooming continuously from Spring to mid-Fall.

Bud:
*Bud shape*.—Globular.
*Bud length*.—Approximately 18 mm.
*Bud diameter*.—Approximately 20 mm.
*Bud color*.—Near Yellow-Green 145C streaked 145B.
Inflorescence:
*Form*.—Terminal capitulum consisting of numerous disc florets, one or two rows of ray florets and two rows of involucral bracts. Plants form the second row of ray florets at approximately 8 to 9 months of age. Plants more than 1 year old form inflorescences with a double row of ray florets.
Flower:
*Diameter of entire inflorescence*.—10 to 12 cm.
*Depth of inflorescence*.—Approximately 3.5 cm.
*Disc diameter*.—Approximately 2.2 cm.
*Receptacle shape*.—Conical.
*Receptacle height*.—Average 1.5 cm.
*Receptacle diameter*.—Average 1.0 cm at base, apex near 4 mm.
*Receptacle color*.—Near RHS White 155A.
*Quantity of inflorescences per lateral stem*.—1.
*Quantity of open inflorescence per plant*.—Average 25 to 35.
*Longevity*.—Average 4 weeks on the plant without significant fading or aging. Persistent.
*Fragrance*.—Faint to moderate earthy scent.
Ray florets:
*Arrangement*.—Rotate. Young plants produce inflorescences with a single row of ray florets. With several months maturity plants produces inflorescences with 2 or 3 rows of ray florets.
*Shape*.—Elliptic.
*Number of ray florets*.—Average range 25 to 35. Single flowers average 11-12.
*Length*.—Approximately 3.5 to 5.5 cm.
*Width*.—Approximately 1.0 to 1.8 cm.
*Apex shape*.—Round with 2, occasionally 3 irregular notches 2-4 mm deep and 2 to 3 mm wide.
*Base*.—Attenuate.
*Margin*.—Entire.
*Texture all surfaces*.—Smooth, matte, ribbed lengthwise.
*Aspect*.—Twisting absent or very weak.
Color:
*Ray florets*.—Upper surface at first opening: Upper approximate 50% near RHS Yellow-Orange 17B, lower 50% Greyed-Orange 175B. Upper surface at maturity: Upper approximate 50% near RHS Yellow-Orange 21A, lower 50% near Greyed-Purple 187B. Under surface at first opening: Near RHS Yellow 6B, lightly flushed Green 143C. Lower 50% flushed Greyed-Red 178A. Under surface at maturity: Near RHS Yellow-Orange 17C. Lower 50% flushed near Greyed-Purple 187A in ridges.
*Disc florets*.—Number of Disc Florets: Approximately 300. Arrangement: Acropetally on disc. Length: Approximately 4 to 6 mm. Width: Approximately 1 mm. Shape: Tubular. Margin: Entire. Apex: Rounded when immature, serrate with age. Base: Fused. Texture: Matte. Color Disc Florets: At first opening: Near RHS Greyed-Purple 187A, base near White 155D. At maturity: Near Greyed-Purple 187B, base near White 155D. Fading: Near Greyed-Purple 187C
Phyllaries/involucral bracts:
*Arrangement*.—Rotate, in 2 rows.
*Number*.—Approximately average range 5 per row to 10 per row.
*Length*.—Average range 10 to 20 mm.
*Width*.—Approximately 3 to 5 mm.
*Shape*.—Lanceolate.
*Apex*.—Acute.
*Base*.—Truncate, fused.
*Margin*.—Entire, ciliate.
*Texture*.—Sericeous upper and lower surfaces.
*Color*.—Inside color near RHS Green 137B. Outside color near RHS Yellow-Green 144A.
Peduncle:
*Length*.—Average range 7 to 10 cm.
*Width*.—Average 5 mm.
*Texture*.—Hispid.
*Color*.—Near RHS Yellow-Green 144B.
*Strength*.—Very strong.

REPRODUCTIVE ORGANS

Ray florets:
Gynoecium: Not present.
Androecium: Not present.
Disc florets:
Androecium:
*Stamen number*.—2.
*Filament length*.—Average 2-3 mm.
*Filament color*.—Near Greyed-Purple 187A.
*Anther shape*.—Forked/curled.
*Anther length*.—0.5 mm.
*Anther color*.—RHS Greyed-Purple 187A.
*Pollen amount*.—Abundant.
*Pollen color*.—Near RHS Yellow-Orange 17A.
Gynoecium:
*Pistil length*.—Approximately 3 mm.
*Stigma shape*.—Decurrent.
*Stigma color*.—Near RHS Greyed-Purple 187A.
*Style length*.—About 2 mm.
*Style color*.—Lower section near RHS White 155C, upper section near Greyed-Purple 187A..
*Ovary color*.—Near RHS White 155C.

OTHER CHARACTERISTICS

Disease resistance: Neither resistance nor susceptibility to diseases or pests normal to *Rudbeckia* have been observed in this variety.
Drought tolerance and temperature tolerance: Hardy perennial, low temperature tolerance to USDA Zone 4, at least. Tolerates high temperature extremely well, to at least 35° C. Some drought tolerance. Plants can be allowed in dry soil for several days without damage.
Fruit/seed production: Not observed to date.

What is claimed is:

1. A new and distinct cultivar of *Rudbeckia* plant named 'G16223' as herein illustrated and described.

* * * * *